(12) United States Patent
Moskovich et al.

(10) Patent No.: US 9,936,796 B2
(45) Date of Patent: Apr. 10, 2018

(54) TOOTHBRUSH

(71) Applicant: COLGATE-PALMOLIVE COMPANY, New York, NY (US)

(72) Inventors: Robert Moskovich, East Brunswick, NJ (US); Kelly Gail Duncan, Washington, NJ (US); Matthew Lee Kolb, Upper Black Eddy, PA (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/106,410

(22) PCT Filed: Dec. 18, 2013

(86) PCT No.: PCT/US2013/076162
§ 371 (c)(1),
(2) Date: Jun. 20, 2016

(87) PCT Pub. No.: WO2015/094231
PCT Pub. Date: Jun. 25, 2015

(65) Prior Publication Data
US 2016/0331109 A1 Nov. 17, 2016

(51) Int. Cl.
| | |
|---|---|
| *A46B 11/00* | (2006.01) |
| *A61C 19/06* | (2006.01) |
| *A46B 9/04* | (2006.01) |
| *A46B 5/02* | (2006.01) |
| *A61C 17/22* | (2006.01) |
| *A61C 5/90* | (2017.01) |

(52) U.S. Cl.
CPC ............ *A46B 11/001* (2013.01); *A46B 5/021* (2013.01); *A46B 9/04* (2013.01); *A46B 9/045* (2013.01); *A61C 17/227* (2013.01); *A46B 2200/1066* (2013.01); *A61C 5/90* (2017.02); *A61C 19/066* (2013.01)

(58) Field of Classification Search
CPC ............................. A46B 11/001; A61C 19/066
USPC ......................................... 401/198, 199, 202
See application file for complete search history.

(56) References Cited

U.S. PATENT DOCUMENTS

| | | | |
|---|---|---|---|
| 9,237,798 B2 | 1/2016 | Jimenez et al. | |
| 2010/0296859 A1 | 11/2010 | Lerner et al. | |
| 2011/0091835 A1 | 4/2011 | Levine | |
| 2011/0135379 A1* | 6/2011 | Jimenez ................ | A46B 11/00 401/268 |
| 2012/0275841 A1 | 11/2012 | Jimenez et al. | |
| 2013/0291325 A1 | 11/2013 | Jimenez et al. | |

FOREIGN PATENT DOCUMENTS

EP    2 386 264    11/2011

* cited by examiner

*Primary Examiner* — David Walczak
*Assistant Examiner* — Joshua Wiljanen

(57) ABSTRACT

A toothbrush having an applicator for applying an oral care material to a users oral cavity. In one aspect, the toothbrush comprises a body comprising a handle portion and a head portion; a plurality of tooth cleaning elements extending from the head portion; and a treatment device detachably coupled to the body so as to be alterable between a storage state and a use state, the treatment device comprising: a housing; a store of an oral care material in the housing; an applicator fluidly coupled to the store of the oral care material; and a bite guard protruding from the housing adjacent the applicator.

19 Claims, 11 Drawing Sheets

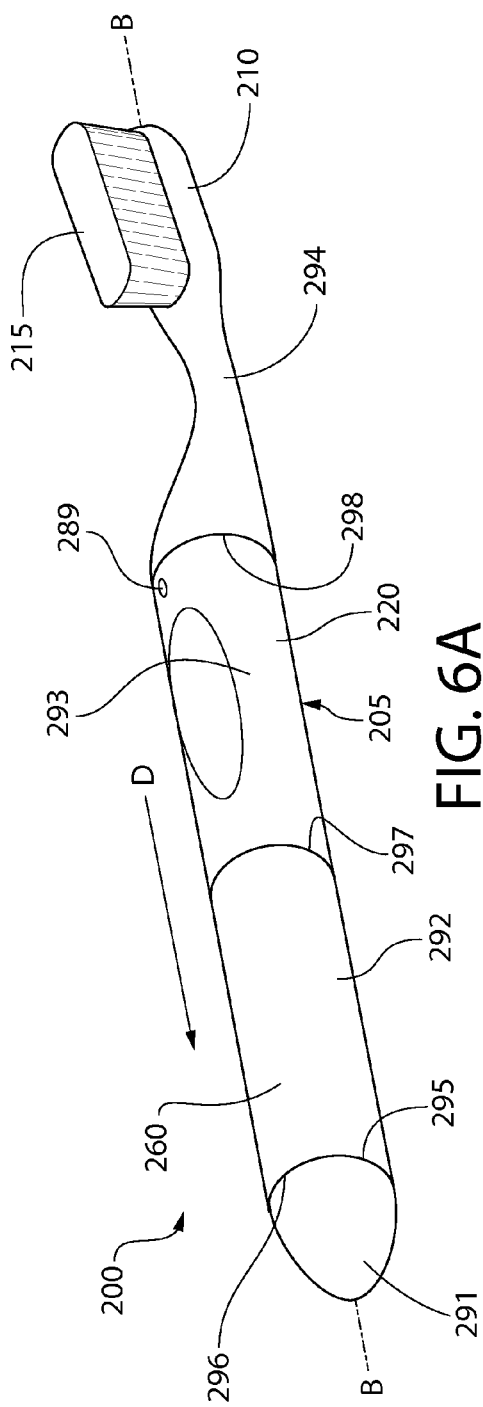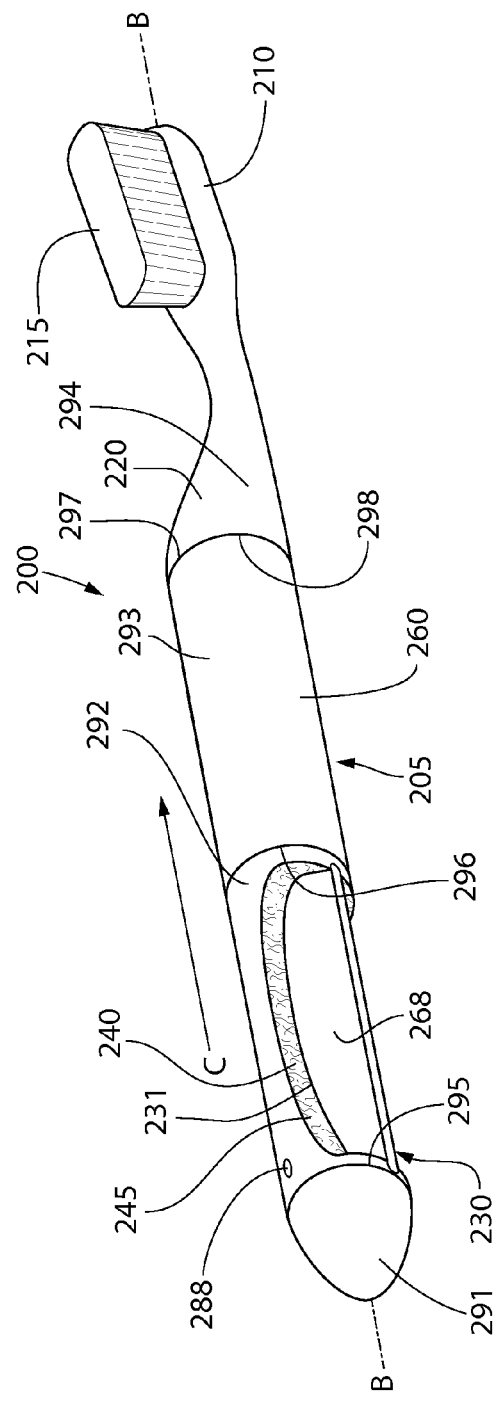

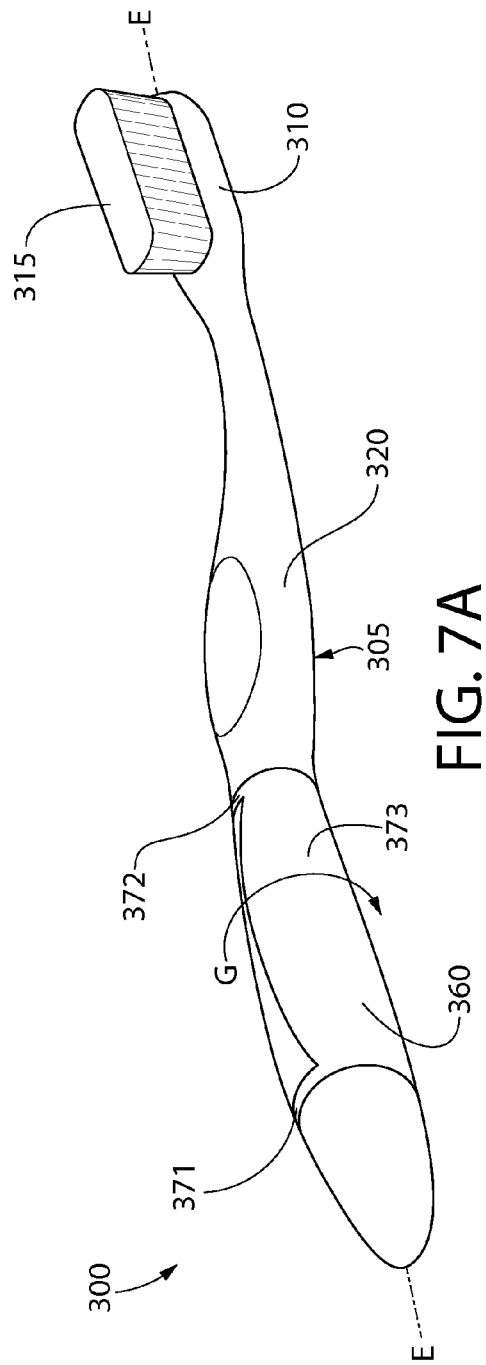
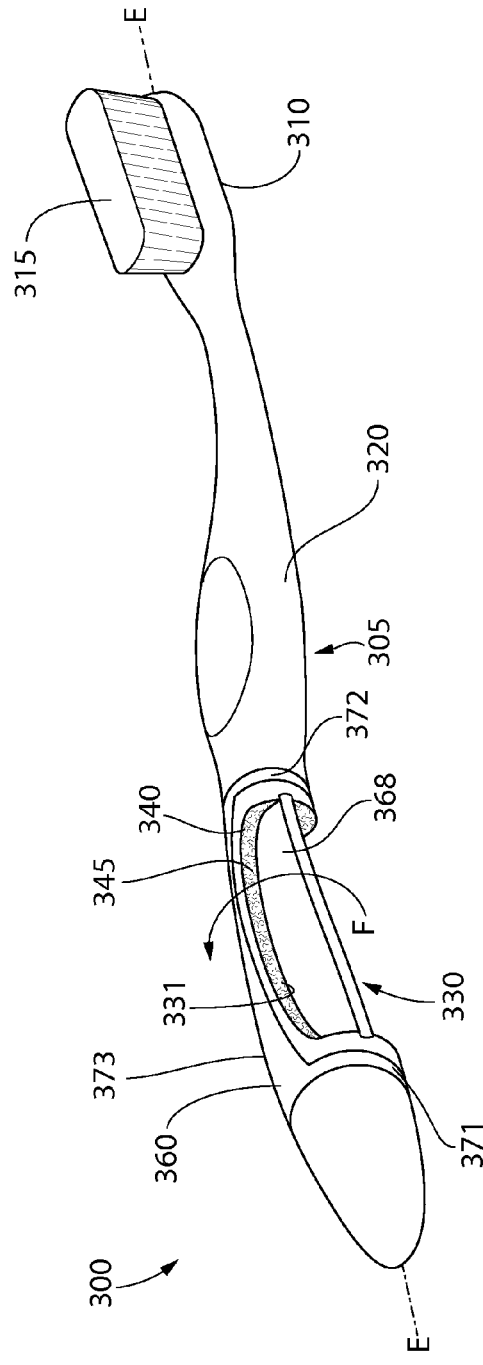

TOOTHBRUSH

BACKGROUND

Oral care implements such as toothbrushes are typically used by applying toothpaste or dentifrice to a bristle section on the head of the toothbrush, followed by brushing regions of the oral cavity (e.g., the teeth or soft tissue such as the tongue and/or gums) with the bristle section. Furthermore, a growing cosmetic trend has been to supplement toothbrushing with the application of additional oral care agents to the user's oral cavity. However, conventional systems for applying oral care agents requires that the user maintain both a toothbrush and an additional kit for storing and dispensing the oral care agent into the user's oral cavity. This not only requires extra storage space in already cramped bathroom cabinets, but also requires that the user remember to use the oral care agent treatment system. Furthermore, these systems are not conveniently portable for transport and/or travel. Moreover, these known systems only apply the oral care agent onto a single tooth at a time, thereby resulting in the application of the oral care agent being a time consuming and ineffective process. These problems require a better way to deliver the oral care agents to the oral cavity and a more convenient oral care agent application system for transport and/or travel.

BRIEF SUMMARY

Exemplary embodiments according to the present disclosure are directed to a toothbrush having an applicator that is fluidly coupled to a store of an oral care material to dispense the oral care material to the user's oral cavity. In some embodiments the applicator forms a portion of a floor of a depression that is formed into a handle portion of the toothbrush. In certain embodiments a bite guard protrudes from the body at a location adjacent to the applicator. In still other embodiments the toothbrush includes a cover that is alterable between a storage state and a use state. In certain embodiments, the toothbrush comprises a body and a treatment device that is detachably coupled to the body. In such embodiments the treatment device includes an applicator, and in some instances also a bite guard. The applicator may have a concave exposed surface that matches the collective facial surfaces of a user's teeth for application of an oral care material onto the facial surfaces of the user's teeth.

In one embodiment, the invention can be a toothbrush comprising a body comprising a handle portion, a head portion and a longitudinal axis; a plurality of tooth cleaning elements extending from the head portion; a store of an oral care material in the body; a depression formed in the handle portion of the body, the depression comprising a floor; and an applicator forming at least a portion of the floor of the depression, the applicator fluidly coupled to the store of the oral care material.

In another embodiment, the invention can be a toothbrush comprising a body comprising a handle portion and a head portion; a plurality of tooth cleaning elements extending from the head portion; a store of an oral care material in the body; an applicator coupled to the body, the applicator fluidly coupled to the store of the oral care material; and a bite guard protruding from the body adjacent the applicator.

In yet another embodiment, the invention can be a toothbrush comprising a body comprising a handle portion and a head portion; a plurality of tooth cleaning elements extending from the head portion; a store of an oral care material in the body; a depression formed in the body, the depression extending from a first outer surface of the body to a second outer surface of the body, the second outer surface of the body being opposite to the first outer surface of the body; and an applicator disposed in the depression, the applicator fluidly coupled to the store of the oral care material.

In a further embodiment, the invention can be a toothbrush comprising a body comprising a handle portion and a head portion; a plurality of tooth cleaning elements extending from the head portion; and a treatment device detachably coupled to the body so as to be alterable between a storage state and a use state, the treatment device comprising: a housing; a store of an oral care material in the housing; an applicator fluidly coupled to the store of the oral care material; and a bite guard protruding from the housing adjacent the applicator.

In a still further embodiment, the invention can be a toothbrush comprising a body comprising a handle portion and a head portion; a plurality of tooth cleaning elements extending from the head portion; and a treatment device detachably coupled to the body so as to be alterable between a storage state and a use state, the treatment device comprising: a housing; a store of an oral care material in the housing; and an applicator fluidly coupled to the store of the oral care material, the applicator comprising a concave exposed surface that forms at least a portion of an inner surface of the treatment device.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 6A is a perspective view of a toothbrush having a body and a cover slidably coupled thereto in accordance with a second embodiment of the present invention, wherein the cover is in a storage state;

FIG. 6B is a perspective view of the toothbrush of FIG. 6A with the cover in a use state;

FIG. 7A is a perspective view of a toothbrush having a body and a cover rotatably coupled thereto in accordance with a third embodiment of the present invention, wherein the cover is in a storage state;

FIG. 7B is a perspective view of the toothbrush of FIG. 7A with the cover in a use state;

DETAILED DESCRIPTION

Figure 1:
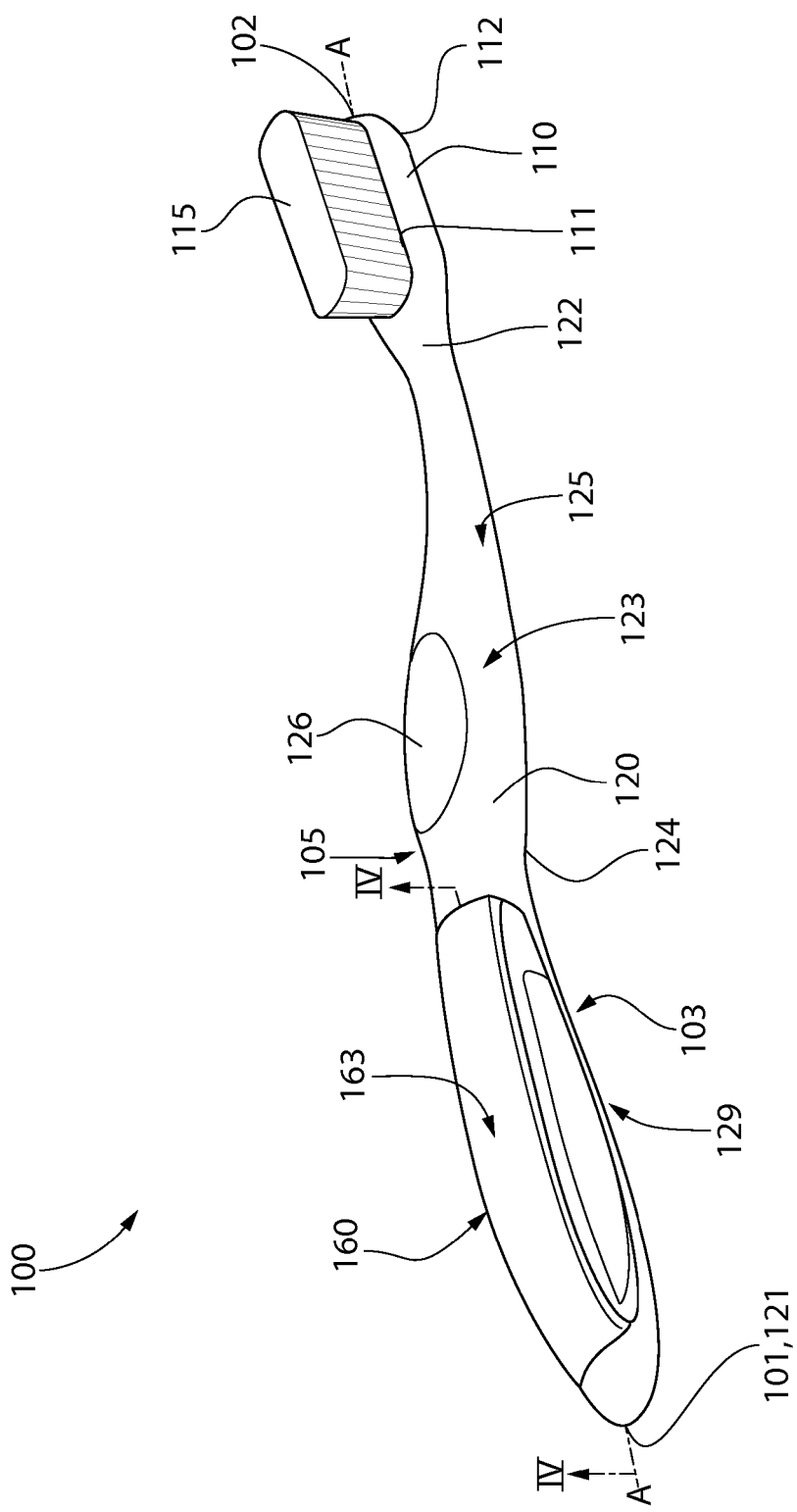
FIG. 1 is a perspective view of a toothbrush having a body and a cover coupled thereto in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
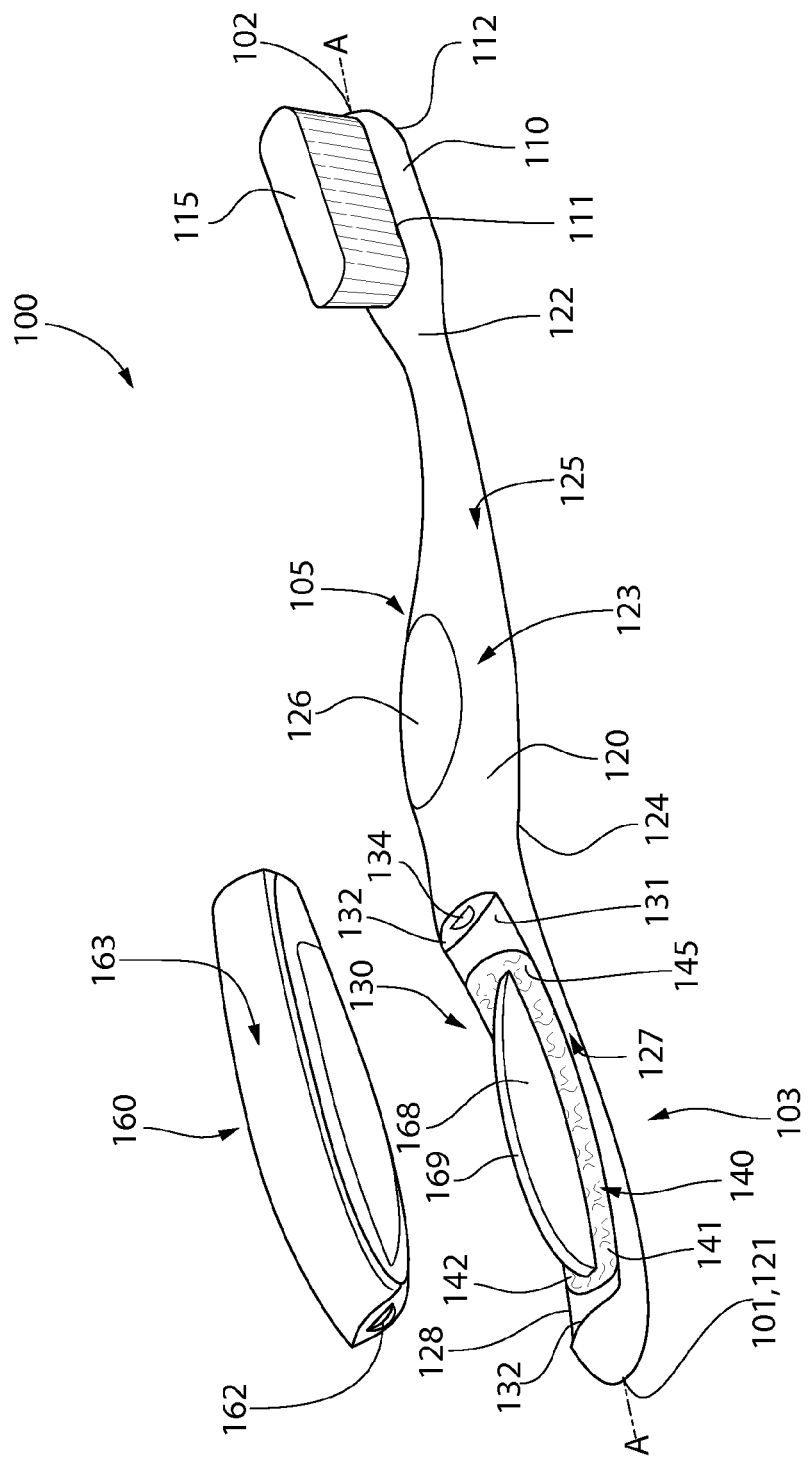
FIG. 2 is a perspective view of the toothbrush of FIG. 1 with the cover separated from the body.

Referring first to FIGS. 1 and 2 concurrently, an oral care implement 100 is illustrated in accordance with an embodiment of the present invention. The oral care implement 100 generally comprises a body 105 comprising a handle portion 120 and a head portion 110, tooth cleaning elements 115 extending from the head portion 110, and a cover 160 coupled to the body 105. The oral care implement 100 is intended to be used such that the tooth cleaning elements 115 clean a user's teeth. Furthermore, the cover 160 is alterable between a storage state (FIG. 1) and a use state (FIG. 2), which will be described in more detail below. When the cover 160 is in the use state, an applicator 140 is exposed and the applicator 140 can be used to apply or dispense an oral care material to a user's teeth or other surfaces of the user's oral cavity. When the cover 160 is in the storage state, the applicator 140 is enclosed by the cover 160 to prevent drying out of the oral care material and to protect the applicator 140 against potential damage. When the cover 160 is in the storage state, the cover 160 and the handle portion 120 of the body 105 collectively form a handle 129 that can be comfortably gripped by a user during toothbrushing.

In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements or any other type of implement that is commonly used for oral care. Thus, it is to be understood that the inventive concepts discussed herein can be applied to any type of oral care implement unless a specific type of oral care implement is specified in the claims.

The body 105 of the oral care implement 100 generally extends from a proximal end 101 to a distal end 102 along a longitudinal axis A-A. Conceptually, the longitudinal axis A-A is a reference line that is generally coextensive with the three-dimensional center line of the body 105. Because the body 105 may, in certain embodiments, be a non-linear structure, the longitudinal axis A-A of the body 105 may also be non-linear in certain embodiments. However, the invention is not to be so limited in all embodiments and in certain other embodiments the body 105 may have a simple linear arrangement and thus a substantially linear longitudinal axis A-A.

As noted above, the body 105 of the oral care implement 100 generally comprises the head portion 110 and the handle portion 120. The handle portion 120 is an elongated structure extending from a proximal end 121 (which is also the proximal end 101 of the body 105) to a distal end 122. The handle portion 120 provides the mechanism by which the user can hold and manipulate the oral care implement 100 during use. The handle portion 120 comprises an outer surface 125 that includes a front surface 123, an opposing rear surface 124, a right-side surface 127 and an opposing left-side surface 128. In the exemplified embodiment, the handle portion 120 is generically depicted having various contours for user comfort. Of course, the invention is not to be so limited in all embodiments and in certain other embodiments the handle portion 120 can take on a wide variety of shapes, contours and configurations, none of which are limiting of the present invention unless so specified in the claims. In one particular embodiment, the handle portion 120 has a generally cylindrical shape.

In the exemplified embodiment, the handle portion 120 is formed of a rigid plastic material, such as for example without limitation polymers and copolymers of ethylene, propylene, butadiene, vinyl compounds and polyesters such as polyethylene terephthalate. In other embodiments the handle portion 120 can be formed of any material that is not incompatible with an oral care material that is stored therein. Of course, the invention is not to be so limited in all embodiments and the handle portion 120 may include a resilient material, such as a thermoplastic elastomer, as a grip cover that is molded over portions of or the entirety of the handle portion 120 to enhance the gripability of the handle portion 120 during use. For example, portions of the handle portion 120 that are typically gripped by a user's palm during use may be overmolded with a thermoplastic elastomer or other resilient material to further increase comfort to a user.

The head portion 110 of the oral care implement 100 is coupled to the handle portion 120 and comprises a front surface 111 and an opposing rear surface 112. Specifically, the head portion 110 of the oral care implement 100 is coupled to the distal end 122 of the handle portion 120. In the exemplified embodiment, the head portion 110 is formed integrally with the handle portion 120 as a single unitary structure using a molding, milling, machining or other suitable process. Thus, in such embodiments the body 105 including both the handle portion 120 and the head portion 110 is formed from a single shot in an injection molding process or in any other manner known in the art. However, in other embodiments the handle portion 120 and the head portion 110 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Typically, the head portion 110 is formed of any of the materials described above for use in forming the handle portion 120.

In the exemplified embodiment, the head portion 110 of the oral care implement 100 is provided with a plurality of tooth cleaning elements 115 extending from the front surface 111. Furthermore, in the exemplified embodiment the tooth cleaning elements 115 are generically illustrated. In certain embodiments the exact structure, pattern, orientation and material of the tooth cleaning elements 115 are not to be limiting of the present invention. Thus, as used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 115 of the present invention can be connected to the head portion 110 in any manner known in the art. For example, staples/anchors, in-mold tufting (IMT) or anchor free tufting (AFT) could be used to mount the cleaning elements/tooth engaging elements to the head portion 110. In certain embodiments, the invention can be practiced with various combinations of stapled, IMT or AFT bristles. In AFT, a plate or membrane having tuft holes therein is formed separately from the body 105 of the oral care implement 100. Bristles or other tooth cleaning elements are positioned within the tuft holes. The free ends of the bristles on one side of the plate or membrane perform the cleaning function. The ends of the bristles on the other side of the plate or membrane are melted together by heat to be anchored in place. After the bristles are properly coupled to the head plate, the head plate is secured to the brush head such as by ultrasonic welding. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

Although not illustrated herein, in certain embodiments the head portion 110 may also include a soft tissue cleanser coupled to or positioned on its rear surface 112. An example of a suitable soft tissue cleanser that may be used with the present invention and positioned on the rear surface 112 of the head portion 110 is disclosed in U.S. Pat. No. 7,143,462, issued Dec. 5, 2006 to the assignee of the present application, the entirety of which is hereby incorporated by reference. In certain other embodiments, the soft tissue cleanser may include protuberances, which can take the form of elongated ridges, nubs, or combinations thereof. Of course, the invention is not to be so limited and in certain embodiments the oral care implement 100 may not include any soft tissue cleanser.

Still referring to FIGS. 1 and 2 concurrently, the oral care implement 100 will be further described. As discussed above, in addition to the body 105, the oral care implement 100 also comprises the cover 160, which is coupled to the body 105. More specifically, the cover 160 is coupled to the body 105 so as to be alterable between a storage state (FIG. 1) and a use state (FIG. 2). In the exemplified embodiment, the cover 160 is detachably coupled to the body 105 such that the cover 160 can be completely separated from the body 105 when the cover 160 is in the use state as depicted in FIG. 2. However, the invention is not to be so limited in all embodiments and in certain other embodiments the cover 160 may be coupled to the body 105 in both the storage and use states, such as by being attached by a hinge or the like so that the cover 160 is hingedly or pivotally coupled to the body 105. In other embodiments, the cover 160 may be slidably coupled to the body 105 so that the cover 160 can be translated longitudinally between the storage and use states (as discussed in more detail below with reference to FIGS. 6A and 6B). In still other embodiments, the cover 160 can be rotatably coupled to the body 105 (as discussed in more detail below with reference to FIGS. 7A and 7B).

The handle portion 120 of the body 105 comprises a depression 130 formed therein. Furthermore, an applicator 140 is disposed in the depression 130. When the cover 160 is in the storage state, the cover 160 is coupled to the handle portion 120 so as to enclose the depression 130 and the applicator 140. When the cover 160 is in the use state, the depression 130 and the applicator 140 are exposed so that the depression 130 or the applicator 140 disposed therein can be used to apply an oral care material to a user's teeth or other oral surfaces.

In the exemplified embodiment, the depression 130 is located in a proximal section 103 of the handle portion 120. More specifically, the depression 130 is located adjacent the proximal end 121 of the handle portion 120 and extends to a location adjacent a thumb grip portion 126 of the handle portion 120. The depression 130 may extend for approximately ¼ of the length of the handle portion 120, approximately ⅓ of the length of the handle portion 120, approximately ½ of the length of the handle portion 120, approximately ¾ of the length of the handle portion 120, or within a range of ¼ to ¾ of the length of the handle portion 120, a range of ¼ to ½ of the length of the handle portion 120, a range of ⅓ to ½ of the length of the handle portion 120, or the like.

Of course, the invention is not to be so limited in all embodiments and the depression 130 may be positioned at other locations along the handle portion 120 of the body 105 and may extend for longer or shorter lengths along the handle portion 120. Furthermore, although in the exemplified embodiment the depression 130 is illustrated as being formed into the front surface 123 of the handle portion 120, the invention is not to be so limited in all embodiments and in certain other embodiments the depression 130 may be formed into the rear surface 124 of the handle portion 120 or any other portions (such as one of the right and left-side surfaces 127, 128) of the outer surface 125 of the handle portion 120 as desired. In other embodiments the depression 130 may be located on the rear surface 112 of the head portion 110. In the exemplified embodiment, the depression 130 forms a recess or cutout into the outer surface 125 of the handle portion 120 within which the cover 160 nests when the cover 160 is in the storage state.

In the exemplified embodiment, the depression 130 extends axially in a direction of the longitudinal axis A-A along the length of the handle portion 120 of the body 105. Furthermore, as noted above the depression 130 is formed into the front surface 123 of the handle portion 120 of the body 105. In certain embodiments, the depression 130 extends from a first outer surface of the body 105 to a second outer surface of the body 105, the second outer surface of the body 105 being opposite to the first outer surface of the body 105. In the exemplified embodiment, this is depicted by the depression 130 extending from the right-side surface 127 of the handle portion 120 of the body 105 to the left-side surface 128 of the handle portion 120 of the body 105. However, in other embodiments whereby the depression 130 is formed into one of the right and left-side surfaces 127, 128 of the handle portion 120 of the body 105, the depression 130 may extend from the front surface 123 of the handle portion 120 of the body 105 to the opposing rear surface 124 of the handle portion 120 of the body 105.

The depression 130 comprises a floor 131 and upstanding sidewalls 132 that extend from the floor 131 to the outer surface 125 of the handle portion 120. Furthermore, as noted above the applicator 140 is disposed in the depression 130. Of course, in certain embodiments the applicator 140 may merely be coupled to the body 105 without the specific location of the applicator 140 being limiting of the invention. In certain embodiments the applicator 140, and more specifically an exposed surface 145 of the applicator 140, may form at least a portion of the floor 131 of the depression 130 and in certain other embodiments the applicator 140 may be positioned atop of the floor 131 of the depression 130. In the exemplified embodiment, each of the floor 131 of the depression 130 and the exposed surface 145 of the applicator 140 is concave along a direction of the longitudinal axis A-A. Of course, the invention is not to be so limited in all embodiments and in certain other embodiments the floor 131 of the depression 130 and the exposed surface 145 of the applicator 140 may be convex or flat.

The concavity of the floor 131 of the depression 130 and of the exposed surface 145 of the applicator 145 may have a contour that corresponds to the contour of the collective facial surfaces of a user's teeth. This may be the contour of the collective labial surfaces of the user's teeth or the contour of the collective labial and buccal surfaces of the user's teeth. Thus, when the applicator 145 is positioned adjacent to the facial surfaces of a user's teeth, the exposed surface 145 of the applicator 140 will contact the facial surfaces of multiple (or all) of the user's teeth simultaneously to dispense or otherwise apply an oral care material to the facial surfaces of the user's teeth in order to impart hygienic benefits to the user's teeth. Thus, the exposed surface 145 of the applicator 140 may be sized and shaped to simultaneously contact a collection of facial surfaces of a user's teeth.

In the exemplified embodiment, the depression 130 further includes a connector 134 on each of the upstanding sidewalls 132 for coupling the cover 160 to the handle portion 120. Although only one connector 134 is visible in FIG. 2, it can be seen from FIG. 4 that in the exemplified embodiment there is a connector 134 on each of the opposing sidewalls 132. Of course, the number and exact location of the connectors 134 are not to be limiting in all embodiments. Furthermore, in the exemplified embodiment the connector 134 is an opening or notch. Of course, the invention is not to be so limited in all embodiments and in certain other embodiments the connector 134 can be a bump or protrusion. In still other embodiments the connector 134 can be a part of a hook-and-loop fastener system or any other type of mechanical coupling system or device. Regardless of the exact configuration of the connectors 134, they are intended to facilitate coupling between the cover 160 and the handle portion 120 so that the cover 160 can be altered between the storage and use states. Alternatively, the connector 134 may be omitted in some embodiments and in such embodiments the cover 160 may couple to the body 105 via a friction or interference fit.

In the exemplified embodiment, the oral care implement 100 further comprises a bite guard 168 protruding from the floor 131 of the depression 130. In the exemplified embodiment, the bite guard 168 extends substantially perpendicular to the floor 131 of the depression 130. The bite guard 168 protrudes from the floor 131 of the depression 130 at a location adjacent to the applicator 140. In one specific embodiment, the depression 130 may be omitted and the oral care implement 100 may merely comprise the applicator 140 as discussed above and the bite guard 168 positioned adjacent to the applicator 140.

In the exemplified embodiment, the applicator 140 comprises a first applicator portion 141 and a second applicator portion 142 and the bite guard 168 is located between the first and second applicator portions 141, 142. Thus, if the user clenches the bite guard 168 between his or her upper and lower teeth, the first applicator portion 141 will be in contact with the facial surfaces of the user's upper teeth and the second applicator portion 142 will be in contact with the facial surfaces of the user's lower teeth. As will be discussed in more detail below, the applicator 140 is in fluid contact with a store of an oral care material. Thus, when the applicator 140 (specifically the first and second applicator portions 141, 142) is in contact with the user's teeth, the applicator 140 dispenses or otherwise applies the oral care material to the user's upper and lower teeth (and specifically to the facial surfaces of the user's upper and lower teeth, which may be only the labial surfaces or the combination of the labial and buccal surfaces of the user's upper and lower teeth).

In the exemplified embodiment, the bite guard 168 is a semi-circle shaped feature that extends from the floor 131 of the depression 130 along the longitudinal axis A-A and terminates in a free edge 169. The free edge 169 of the bite guard 168 is arcuate shaped and forms a convex edge of the bite guard 168. Although illustrated as being semi-circle shaped, the invention is not to be so limited and the shape of the bite guard 168 may be other than semi-circular, such as rectangular, triangular or any other polygonal shape. In still other embodiments the bite guard 168 may simply be a thin cylindrical protrusion that extends from the floor 131 of the depression 130 that can be gripped between a user's teeth and/or lips during use as will be discussed in more detail below.

Thus, the size and/or shape of the bite guard 168 are not to be limiting of the present invention in all embodiments. In certain embodiments it is merely desirable that the bite guard 168 is configured to enable a user to maintain the applicator 140 in a location adjacent to the facial surfaces of a user's teeth during tooth whitening or other oral hygiene operations such as by gripping the bite guard 168 between the user's upper and lower teeth or between the user's upper and lower lips. Furthermore, in still other embodiments the bite guard 168 may be altogether omitted. In such embodiments the applicator 140 can be held up to a user's teeth by a user gripping the handle portion 120 of the body 105 of the oral care implement 100 and manipulating the oral care implement 100 as desired.

In certain embodiments the bite guard 168 may be formed integrally with the body 105 of the oral care implement 100 such that the bite guard 168 is formed out of the same material as the body 105 of the oral care implement 100. Of course, the invention is not to be so limited and in certain other embodiments the bite guard 168 may be a separate component that is coupled or molded to the body 105 of the oral care implement 100. For example, the body 105 of the oral care implement 100 may be formed of a rigid or hard plastic material such as one of the materials discussed above and the bite guard 168 may be formed of a rubber material, such as a thermoplastic elastomer, an unsaturated rubber, a saturated rubber or the like. In such embodiments, the bite guard 168 can be coupled to the body 105 of the oral care implement 100 via mechanical interlocking features in the molding of the body 105 of the oral care implement 100 and the bite guard 168, or by adhesion, fasteners or the like. Forming the bite guard 168 out of a thermoplastic elastomer (or other rubber material) is desirable in some embodiments because it is more comfortable for a user to grip a thermoplastic elastomer between his or her teeth and/or lips than it is to grip a rigid plastic material between his or her teeth and/or lips. In certain other embodiments as discussed in more detail below, the bite guard 168 may be formed out of a capillary material.

Figure 3:
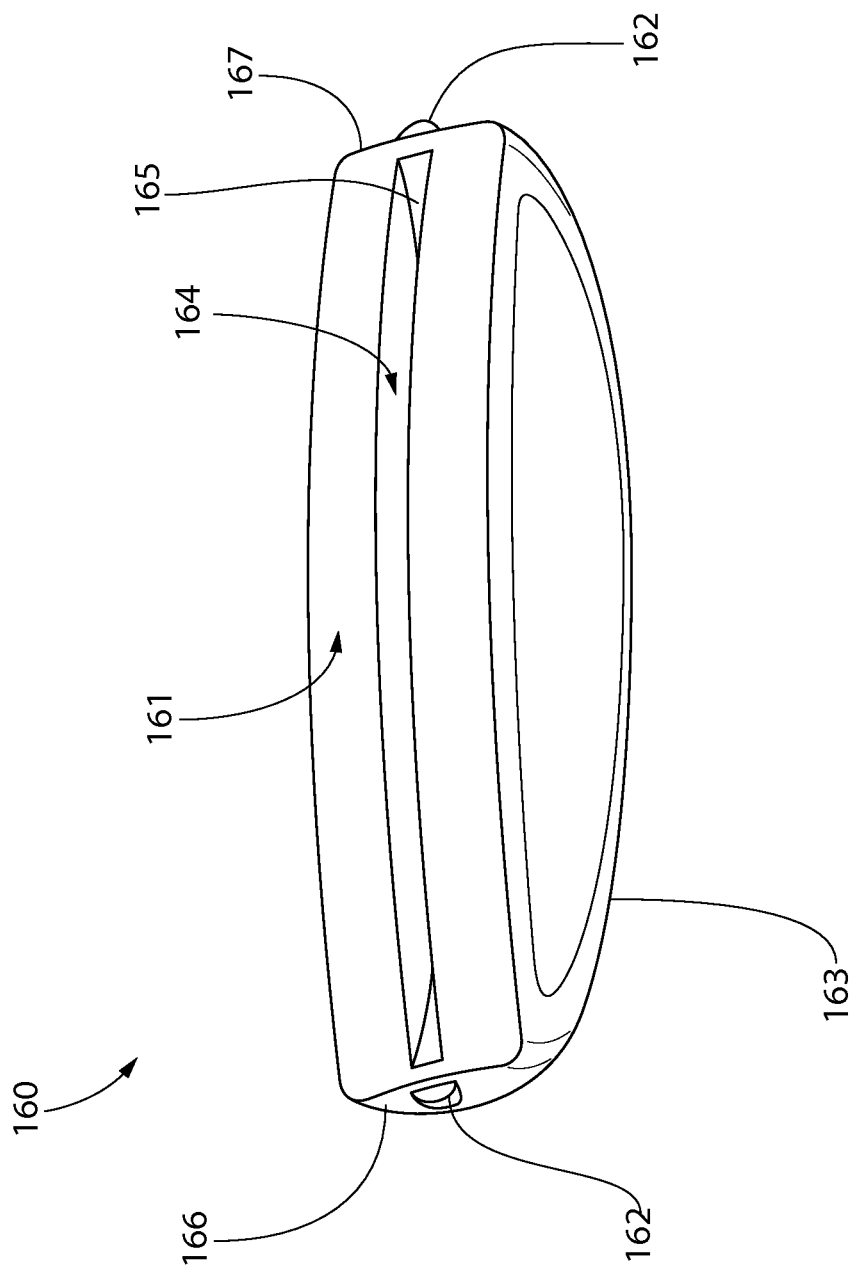
FIG. 3 is a perspective view of the cover of FIG. 1.

Referring now to FIG. 1-3 concurrently, the cover 160 of the oral care implement 100 will be further described. The cover 160 comprises an inner surface 161, an outer surface 163 and opposing sidewall surfaces 166, 167. In the exemplified embodiment, the inner surface 161 of the cover 160 is convex to facilitate the cover 160 nesting within the depression 130 as will be discussed in more detail below with reference to FIGS. 4 and 5. A slot 164 is formed into the inner surface 161 of the cover 160 that extends along a portion of the length of the cover 160. Specifically, the slot 164 is longitudinally elongated along the inner surface 164 of the cover 160. In the exemplified embodiment, the slot 164 does not extend through the entire thickness of the cover 160, but rather the slot 164 has a floor 165. Of course, the invention is not to be so limited in all embodiments and in certain other embodiments the slot 164 may extend through the entire thickness of the cover 160 (from the inner surface 164 to the outer surface 163) so as to form a passageway through the cover 160. The slot 164 is sized and shaped to enable the bite guard 168 to nest therein when the cover 160 is in the storage state. In embodiments whereby the bite guard 168 is omitted, the slot 164 may also be omitted.

In the exemplified embodiment, the cover 160 comprises a connector 162 extending from each of the opposing sidewall surfaces 166, 167 of the cover 160. Specifically, in the exemplified embodiment each of the connectors 162 is a protrusion that is intended to mate with a corresponding one of the connectors 134 (i.e., the opening or notch) on the sidewall 134 of the longitudinal depression 130. Of course, in other embodiments the connector 134 may be the protrusion as discussed above and the connector 162 may be a notch or opening. In still other embodiments, the connectors 134, 162 may comprise components of a hook-and-loop fastening system or any other type of mechanical coupling system or device for coupling the cover 160 to the handle portion 120 of the body 105 of the oral care implement 100. Alternatively, the connectors 134, 162 may be altogether omitted and the cover 160 may be coupled to the body 105 via a friction or interference fit.

In certain embodiments, the entire cover 160, including the connector 162, is formed of a rigid plastic material, such as any of the materials discussed above with regard to the handle portion 120. However, due to its small size, the connector 162 is able to have some resiliency/movement to enable the cover 160 to be coupled to and decoupled from the handle portion 120 of the body 105. Specifically, when positioning the cover 160 into and out of the storage state, the connector 162 may move and flex as needed to enable the cover 160 to nest within and be separated from the handle portion 120 of the body 105. In other embodiments, the connector 162 of the cover 160 may be formed of a more resilient material, such as a thermoplastic elastomer.

Referring now to FIGS. 1, 2, 4 and 5 concurrently, the oral care implement 100 will be further described. In the exemplified embodiment, the body 105 of the oral care implement 100 comprises a reservoir 180 containing a store of an oral care material 181. In the exemplified embodiment, the reservoir 180 is located within the handle portion 120 of the oral care implement 100. However, the invention is not to be so limited in all embodiments and in certain other embodiments the reservoir 180 may be located in the head portion 110 of the oral care implement 100 or elsewhere as desired. The exact location of the reservoir 180 is not to be limiting in all embodiments. However, it is desirable that the applicator 140 be fluidly coupled to the store of oral care material 181 so that the oral care material 181 can be applied to a user's teeth and other oral surfaces via the applicator 140.

The reservoir 180 may be replaceable or refillable in certain embodiments. Thus, the oral care implement 100 may include a port with a removable plug that enables an additional amount of the oral care material 181 to be added into the reservoir 180 when the initial amount of the oral care material 181 in the reservoir 180 has been depleted. In some embodiments the oral care implement 100 may include a removable end cap that is coupled to the proximal end of the body 105 via a threaded screw attachment, interference fit, or the like. In such embodiments the end cap can be removed in order to facilitate refilling of the reservoir 180. In other embodiments, the reservoir 180 may be formed as a separate component that is operably coupled to the body 105 of the oral care implement. In such embodiments upon depletion of the oral care material 181 in the reservoir 180, the entire reservoir 180 component may be replaced, or it may simply be refilled as discussed above.

In the exemplified embodiment, the applicator 140 comprises a pad 144 that comprises or is formed of a capillary material. The capillary material of the pad 144 can be any material that is capable of wicking the oral care material 181 from the reservoir 180 and into the pad 144 via capillary action, such as for example without limitation a porous plastic, a ceramic, foam, a sponge, a cloth, synthetic mesh, combinations thereof, or the like. In the exemplified embodiment, the pad 140 is positioned atop of a wall 138 that is recessed relative to the floor 131 of the depression 130 and that forms a roof of the reservoir 180. Thus, the exposed surface 145 of the applicator 140 (and of the pad 144) is flush with and forms a portion of the floor 131 of the depression 130.

The wall 138 prevents direct contact between the pad 140 and the store of oral care material 181. Thus, in the exemplified embodiment one or more wicking members 143 (only some of which are numbered in the drawings to avoid clutter) fluidly couple the pad 144 to the store of oral care material 181. Specifically, in the exemplified embodiment a plurality of the wicking members 143 extend from the pad 144, through passageways 139 formed into the wall 138, and into the store of oral care material 181 contained within the reservoir 180 so that the store of oral care material can be wicked up to the pad 144 via the wicking members 143. Thus, the wicking members 143 may also be formed of one of the capillary materials noted above. The wicking members 143 and the pad 144 may be formed of the same capillary material or different capillary materials as desired. In certain embodiments the wicking members 143 may be formed integrally with the pad 144, although such is not required.

In the exemplified embodiment the reservoir 180 and the store of the oral care material 181 are positioned directly beneath the applicator 140 such that the wicking members 143 simply extend downwardly from the pad 144 through the passageways 139 and into contact with the store of the oral care material 181. However, as noted above the reservoir 180 can be located at any position within the body 105, and thus the wicking members 143 may extend through the body 105 as needed in order to come into contact with the oral care material 181 to wick the oral care material 181 into the pad 144 for dispensing purposes. Thus, for example, if the reservoir 180 is located within the head portion 110 of the body 105, the wicking members 143 may extend through a passageway that leads from the pad 144 all the way to the head portion 110 of the body 105.

Of course, the invention is not to be limited to the structural arrangement depicted in the drawings in all embodiments. In certain other embodiments the pad 144 of the applicator 140 may be in direct contact with the store of oral care material 181. Specifically, in such embodiments the wall 138 may be omitted so that a bottom surface 146 of the pad 144 is in direct contact with the store of oral care material 181. In such embodiments, the wicking members 143 may be omitted because the oral care material 181 will be wicked onto the pad 144 due to the direct contact between the pad 144 and the oral care material 181.

Furthermore, although the applicator 140 is described herein as comprising the pad 144 formed of a capillary material, the invention is not to be so limited in all embodiments. In certain other embodiments the applicator 140 may merely comprise openings that are formed in the floor 131 of the depression 130, or the applicator 140 may comprise a pad formed of a thermoplastic elastomer that is positioned atop of the wall 138 and such pad may include openings formed therethrough. In such an embodiment, the oral care material 181 may be dispensed through the applicator 140 by a user depressing/squeezing the outer surface of the body 105 or by depressing or otherwise actuating an actuator. In one embodiment, the thumb grip 126 may also function as such an actuator such that depressing the thumb grip 126 forces air to enter into the reservoir 180, which in turn forces the oral care material 181 to be dispensed from the reservoir 180 to the applicator 140. Thus, the thumb grip 126 or the body 105 may form an actuator that is configured to deliver the oral care material 181 from the reservoir 180 to the applicator 140.

Furthermore, in certain embodiments the bite guard 168 may also be fluidly coupled to the oral care material 181 contained within the reservoir 180. In some such embodiments, the bite guard 168 may also be formed of a capillary material, such as any of the materials discussed above, to facilitate wicking of the oral care material onto the bite plate 168 via capillary action. In such embodiments the oral care material can be applied or dispensed onto the user's teeth via both the applicator 140 and the bite plate 168.

The oral care material may be any type of material that is desired to be applied to a user's teeth and or other oral surfaces in order to impart benefits to the user's teeth and other oral surfaces. In one embodiment, the oral care material is a tooth whitening agent or solution. In such embodiments any suitable tooth whitening agent can be used, including without limitation peroxide containing tooth whitening compositions. Other whitening agents may include an oxidizer such as for example without limitation carbamide peroxide, carbamyl peroxide, sodium percarbonate, perhydrol urea, peroxyacetic acid, and hydrogen peroxide.

While a tooth whitening agent is one of the preferred oral care materials in the present invention, other oral care materials can be used with the invention. Contemplated oral care materials include without limitation, antibacterial agents; oxidative or whitening agents; enamel strengthening or repair agents; tooth erosion preventing agents; tooth sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. Although in some embodiments the oral care material may be a dentifrice, the oral care material is preferably free of (i.e., is not) dentifrice in some other embodiments. Instead, in such embodiments the oral care material is intended to provide benefits in addition to merely brushing one's teeth. Other suitable oral care materials could include lip balm or other materials that are typically available in a semi-solid state. Furthermore, in still other embodiments the oral care material can be a natural ingredient, such as for example without limitation, lotus seed; lotus flower, bamboo salt; jasmine; corn mint; camellia; aloe; gingko; tea tree oil; xylitol; sea salt; vitamin C; ginger; cactus; baking soda; pine tree salt; green tea; white pearl; black pearl; charcoal powder; nephrite or jade and Ag/Au+.

Figure 4:
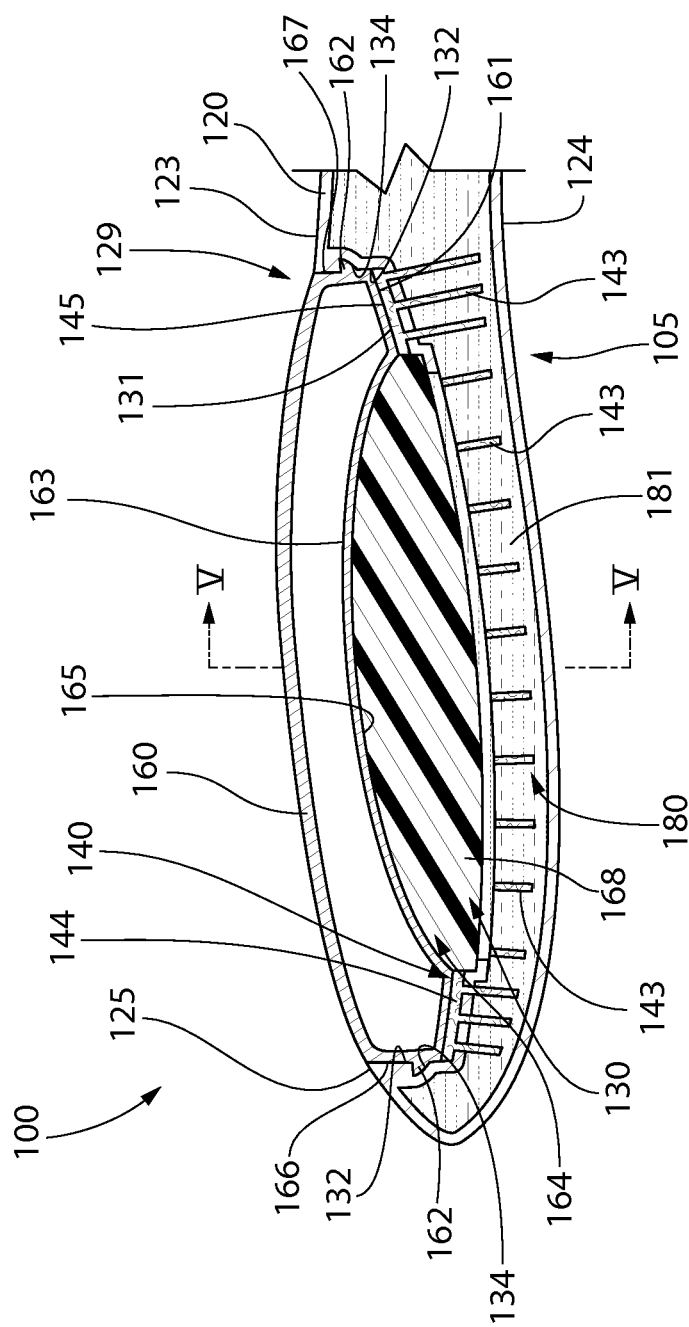
FIG. 4 is a schematic cross-sectional view taken along line IV-IV of FIG. 1.
Figure 5:
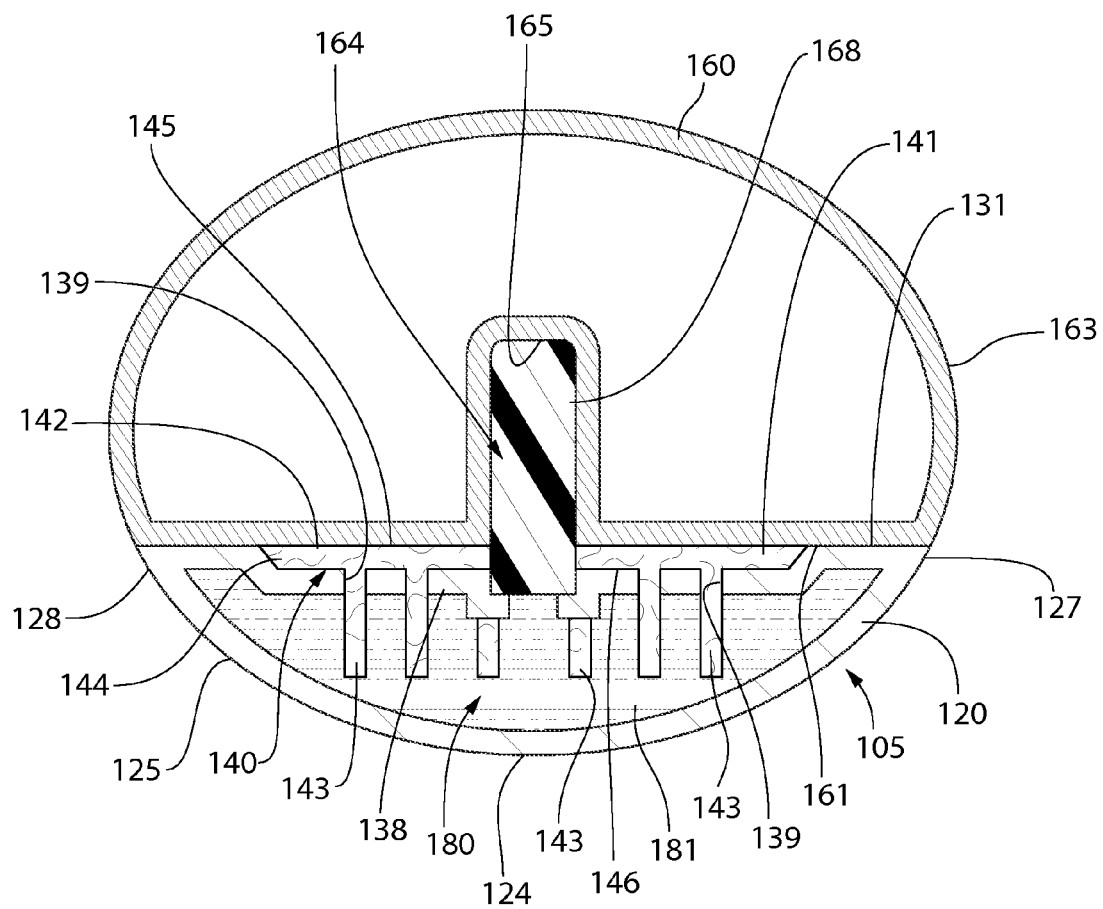
FIG. 5 is a schematic cross-sectional view taken along line V-V of FIG. 4.
Figure 8:
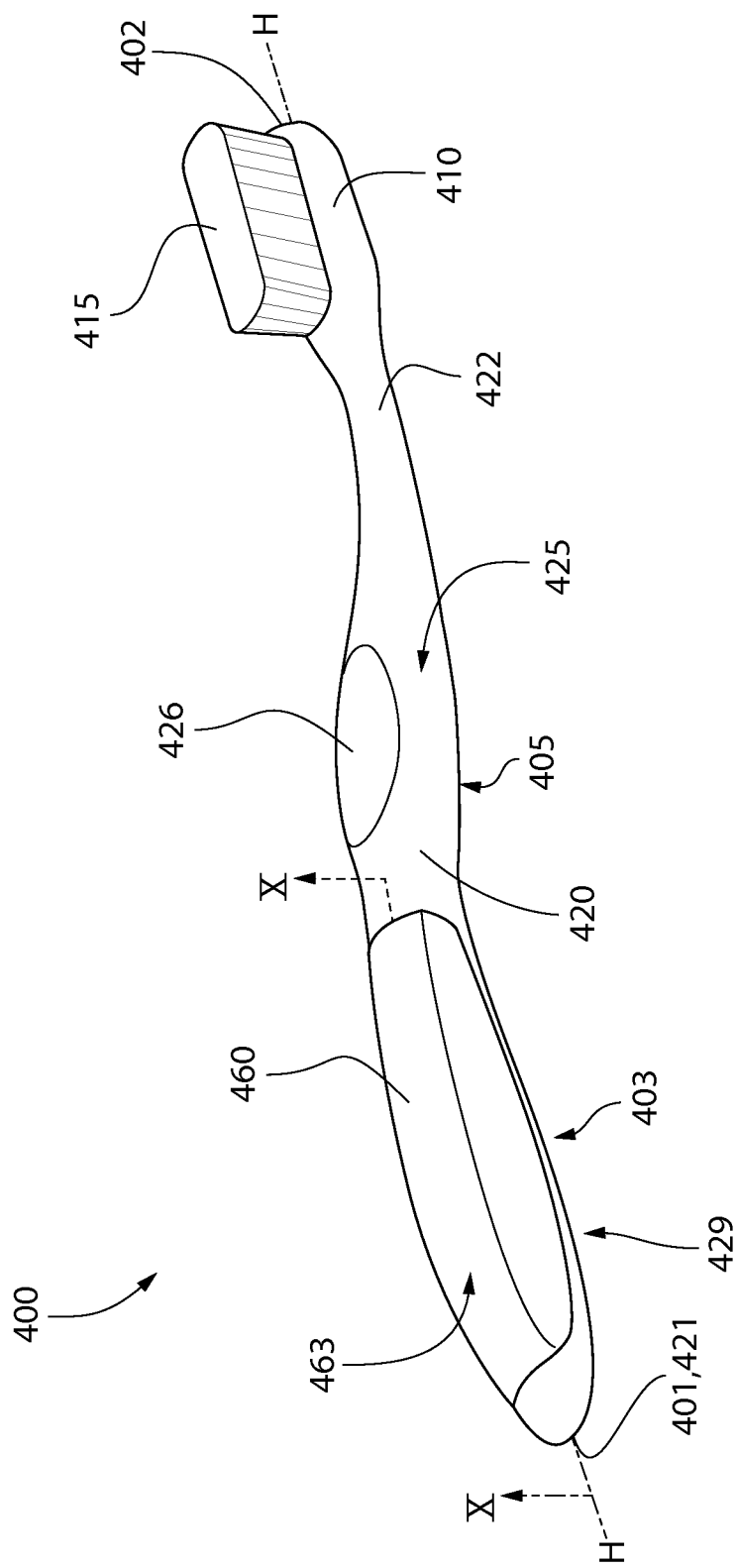
FIG. 8 is a perspective view of a toothbrush having a body and a treatment device coupled thereto in accordance with a fourth embodiment of the present invention.

Referring to FIGS. 4 and 5 concurrently, the oral care implement 100 is depicted with the cover 160 in the storage state such that the cover 160 is coupled to the handle portion 120 of the body 105. In FIGS. 4 and 5 the cover 160 is depicted having a hollow interior cavity. This may be desirable in order to reduce the costs of materials. However, if it is desired to have a more rigid housing, the cover 160 may be formed of a solid structure such that the hollow cavity is filled in with material (i.e., the cover 160 may be devoid of any interior cavity).

When the cover 160 is in the storage state, the cover 160 forms a transverse section of the handle 129 of the oral care implement 100 along a length of the depression 130. Furthermore, when the cover 160 is in the storage state the outer surface 125 of the handle portion 120 is substantially flush with the outer surface 163 of the cover 160. Thus, the combined handle 129 that is formed from the handle portion 120 and the cover 160 when the cover is in the storage state is free of ridges and undulations in the transition regions between the cover 160 and the handle portion 120, which enhances user comfort when a user is handing the oral care implement 100 during toothbrushing or otherwise. Furthermore, when the cover 160 is in the storage state, the inner surface 161 of the cover 160 is in surface contact with the floor 131 of the depression 130 and the bite guard 168 extends into the slot 164 of the cover 160. Forming the inner surface 161 of the cover 160 to be a convex surface and the floor 131 of the depression 130 to be a concave surface facilitates this surface contact relationship between those surfaces, which reduces the size requirements of the oral care implement 100 when the cover 160 is in the storage state.

In the exemplified embodiment, with the cover 160 in the storage state the connectors 162 of the cover 160 cooperate with the connectors 134 of the depression 130 to secure the cover 160 in the storage state. More specifically, in the exemplified embodiment the connectors 162 of the cover 160, which are protrusions, nest within the connectors 134 of the depression 130 of the handle portion 120, which are notches or openings. The connectors 134 further include a flange that extends above the opening to prevent the protrusion of the cover 160 from easily disengaging or being removed from the opening. Thus, a user must apply some amount of force (i.e., pulling the cover 160 and the body 105 in opposite directions) to separate the cover 160 from the longitudinal depression 130 due to the corresponding connectors 134, 162. Although a specific structural arrangement of the connectors 134, 162 is illustrated, the invention is not to be limited by the mechanisms used for securing the cover 160 to the handle portion 120 in all embodiments, and in other embodiments adhesion, fasteners, hook-and-loop fasteners, springs, other mechanical interlocking features or the like can be used to secure the cover 160 to the handle portion 120 in the storage state while enabling the cover 160 to be easily transitioned from the storage state to the use state. Moreover, in one particular embodiment the connectors 134, 162 may be omitted and the engagement between the bite guard 168 and the slot 164 may be an interference or friction fit that facilitates coupling the cover 160 to the handle portion 120 of the body 105 of the oral care implement 100.

The oral care implement 100 can be used as follows. First, the oral care implement 100 can be used in the conventional manner by a user gripping the handle 129 and inserting the head portion 110 of the oral care implement 100 into his or her mouth to clean his or her teeth with the tooth cleaning elements 115. During this toothbrushing, the cover 160 is typically in the storage state as depicted in FIG. 1 so that the handle 129 is provided for comfortable gripping by the user. Either before or after cleaning the user's teeth with the tooth cleaning elements 115 (or at any other desired time), a user may apply the oral care material 181 to the user's teeth. Therefore, when so desired, the cover 160 is detached from the handle portion 120 or otherwise altered into the use state so that the floor 131 of the depression 130 and also the exposed surface 145 of the applicator 140 is exposed for use (see FIG. 2).

Once the exposed surface 145 of the applicator 140 is exposed for use, the exposed surface 145 of the applicator 140 can be held up to and placed into contact with the facial surfaces of the user's teeth. In embodiments that include the bite guard 168, the bite guard 168 can be positioned between the user's upper and lower teeth in order to maintain the exposed surface 145 of the applicator 140 into the desired position into contact with the user's teeth. If the bite guard 168 is not included, the user can simply manipulate the handle portion 120 of the oral care implement 100 to orient the exposed surface 145 of the applicator 140 into contact with the facial surfaces of the user's teeth.

As noted above, the exposed surface 145 of the applicator 140 is a concave surface, and the concave surface may correspond to or match the shape of the facial surfaces of a user's teeth. Thus, in such embodiments when the applicator 140 held adjacent to the user's teeth, the facial surfaces of the user's teeth are in direct surface contact with the exposed surface 145 of the applicator 140. In certain embodiments simply positioning the exposed surface 145 of the applicator 140 into contact with the facial surfaces of the user's teeth will achieve dispensing of the oral care material 181 onto the facial surfaces of the user's teeth due to the capillary action discussed above. Specifically, due to pressure applied directly from the user's teeth onto the exposed surface 145 of the applicator 140, the oral care material 181 may leach out of the applicator 140 and be dispensed onto the user's teeth. This is possible in part because the applicator 140 is formed of a capillary material and the applicator 140 is fluidly coupled to the oral care material 181. However, in other embodiments the user may actuate the actuator, such as by squeezing the body 105 of the oral care implement 100 or depressing the thumb grip 126 or otherwise in order to cause the oral care material 181 to be delivered or pumped from the reservoir 180 to the applicator 140.

After the exposed surface 145 of the applicator 140 has been in contact with the facial surfaces of the user's teeth for a desired period of time, the applicator 140 can be pulled away from the user's teeth and the cover 160 can be replaced back into the storage state to protect the applicator 140 against damage and to prevent the oral care material 181 from drying out or leaking. At this time, the oral care implement 100 can be stowed away until it is desired to repeat the steps discussed above.

Referring to FIGS. 6A and 6B concurrently, an oral care implement 200 is illustrated in accordance with another embodiment of the present invention. The oral care implement 200 is similar to the oral care implement 100 in many respects, and thus similar features will be similarly numbered except that the 200-series of numbers will be used. Certain features of the oral care implement 200 may be similarly numbered as the oral care implement 100 but might not be described in detail herein in the interest of brevity, it being understood that the discussion of the similar component on the oral care implement 100 applies. Furthermore, features of the oral care implement 100 described above that are not illustrated on the oral care implement 200 or that are illustrated on the oral care implement 200 but not numbered are applicable to the oral care implement 200 in certain embodiments and vice versa. Thus, various combinations of the description below with regard to the oral care implement 200 and the description above with regard to the oral care implement 100 are within the scope of the present invention in some embodiments.

The oral care implement 200 generally comprises a body 205 that extends along a longitudinal axis B-B. The body 205 comprises a handle portion 220 and a head portion 210, the head portion 210 having tooth cleaning elements 215 extending therefrom. The body 205 comprises a depression 230 having a floor 231, an applicator 240 having an exposed portion 245, a bite guard 268 and a store of oral care material (not illustrated) that are similar to the features of the oral care implement 100 with the same name described above with reference to FIGS. 1-5. On the oral care implement 200, the depression 230 and the applicator 240 are located on a right-side surface of the handle portion 220 of the body 205. However, the depression 230 and the applicator 240 can be located at any position as discussed above with regard to the oral care implement 100.

The oral care implement 200 also comprises a cover 260 that is coupled to the body 205 of the oral care implement 200 so as to be alterable between a storage state (see FIG. 6A) in which the depression 230 is enclosed by the cover 260 and a use state (see FIG. 6B) in which the floor 231 of the depression 230 and the exposed portion 245 of the applicator 240 is exposed. The main difference between the oral care implement 200 relative to the oral care implement 100 is the shape of the cover 260 and the manner in which the cover 260 is coupled to the handle portion 220 of the oral care implement 200.

Specifically, in the exemplified embodiment the cover 260 is a tubular member that is slidably coupled to the body 205. Thus, the cover 260 is translatable in a direction along the longitudinal axis B-B to alter the cover 260 between the storage and use states. Specifically, translating the cover 260 in the direction of the arrow C of FIG. 6B alters the cover 260 from the storage state to the use state. Translating the cover 260 in the direction of the arrow D of FIG. 6A alters the cover 260 from the use state to the storage state.

The handle portion 220 of the oral care implement 200 comprises a proximal end section 291, a depression section 292, a thumb grip section 293 and a neck section 294. The proximal end section 291 has a first maximum transverse cross-sectional area at its distal edge 295, the depression section 292 has a second maximum transverse cross-sectional area, the thumb grip section 293 has a third maximum transverse cross-sectional area, the neck section 294 has a fourth maximum transverse cross-sectional area at its proximal edge 298 and the cover 260 has a fifth transverse cross-sectional area at its proximal and distal edges 296, 297. The first and fourth maximum transverse cross-sectional areas and the fifth transverse cross-sectional area are substantially the same, or the fifth transverse cross-sectional area may be less than the first and fourth maximum transverse cross-sectional areas. Furthermore, the second and third maximum transverse cross-sectional areas are smaller than each of the first and fourth maximum transverse cross-sectional areas and the fifth transverse cross-sectional area. This difference in the transverse cross-sectional areas of the various portions of the handle portion 220 of the oral care implement 200 and of the cover 260 enables the cover 260 to translate/slide along each of the depression section 292 and the thumb grip section 293 of the handle portion 220 of the oral care implement 200.

More specifically, because the cover 260 has a greater transverse cross-sectional area than each of the depression section 292 and the thumb grip section 293 (stated another way, the interior diameter of the cover 260 is greater than the exterior diameters of each of the depression section 292 and the thumb grip section 293), the cover 260 can circumferentially surround each of the depression section 292 and the thumb grip section 293. Furthermore, because the cover 260 has a length that is substantially equal to the lengths of each of the depression section 292 and the thumb grip section 293, the cover 260 can freely slide therebetween. Thus, when the cover 260 is in the storage state (FIG. 6A), the cover 260 circumferentially surrounds the depression section 292 of the handle portion 220 of the oral care implement 200. However, the cover 260 is prevented from sliding off of the handle portion 220 of the oral care implement 200 because the first maximum transverse cross-sectional area of the distal edge 295 of the proximal end section 291 of the handle portion 220 of the oral care implement 200 is equal to or greater than the fifth transverse cross-sectional area of the proximal edge 296 of the cover 260. Thus, when the cover 260 is in the storage state, the proximal edge 296 of the cover 260 abuts against the distal edge 295 of the proximal end section 291. Thus, the cover 260 is prevented from translating in the direction of the arrow D beyond the distal edge 295 of the proximal end section 291.

Similarly, when the cover 260 is in the use state (FIG. 6B), the cover 260 circumferentially surrounds the thumb grip section 293 of the handle portion 220 of the oral care implement 200. However, the cover 260 is prevented from sliding off of the handle portion 220 of the oral care implement 200 because the fourth transverse cross-sectional area of the proximal edge 298 of the neck section 294 of the handle portion 220 of the oral care implement 200 is equal to or greater than the fifth transverse cross-sectional area of the cover 260. Thus, when the cover 260 is in the use state, the distal edge 297 of the cover 260 abuts against the proximal edge 298 of the neck section 294. Thus, the cover 260 is prevented from translating in the direction of the arrow C beyond the proximal edge 298 of the neck section 294.

Furthermore, the cover 260 has a protuberance or a detent (not visible) on its interior surface that cooperates with a corresponding detent or protuberance on the handle portion 220 of the oral care implement 200 to prevent the cover 260 from freely spinning or rotating about the longitudinal axis B-B when the cover 260 is in either of the storage or use states. Thus, the cooperation between these protuberances and detents secures or locks the cover 260 into the storage and use states. In the exemplified embodiment, a first protuberance or detent 288 is positioned on the depression section 292 of the handle portion 220 of the oral care implement 200 and a second protuberance or detent 289 is positioned on the thumb grip section 293 of the handle portion 220 of the oral care implement 200. When the cover 260 is in the storage state, the protuberance or detent on the interior surface of the cover 260 cooperates with the first protuberance or detent 288 to prevent the cover 260 from freely spinning or rotating about the longitudinal axis B-B. When the cover 260 is in the use state, the protuberance or detent on the interior surface of the cover 260 cooperates with the second protuberance or detent 289 to prevent the cover 260 from freely spinning or rotating about the longitudinal axis B-B.

Referring to FIGS. 7A and 7B concurrently, an oral care implement 300 is illustrated in accordance with another embodiment of the present invention. The oral care implement 300 is similar to the oral care implement 100 in many respects, and thus similar features will be similarly numbered except that the 300-series of numbers will be used. Certain features of the oral care implement 300 may be similarly numbered as the oral care implement 100 but might not be described in detail herein in the interest of brevity, it being understood that the discussion of the similar component on the oral care implement 100 applies. Furthermore, features of the oral care implement 100 described above that are not illustrated on the oral care implement 300 or that are illustrated on the oral care implement 300 but not numbered are applicable to the oral care implement 300 in certain embodiments and vice versa. Thus, various combinations of the description below with regard to the oral care implement 300 and the description above with regard to the oral care implement 100 are within the scope of the present invention in some embodiments.

The oral care implement 300 generally comprises a body 305 that extends along a longitudinal axis E-E. The body 305 comprises a handle portion 320 and a head portion 310, the head portion 310 having tooth cleaning elements 315 extending therefrom. The body 305 comprises a depression 330 having a floor 331, an applicator 340 having an exposed portion 345, a bite guard 368 and a store of oral care material (not illustrated) that are similar to the features of the oral care implement 100 with the same name described above with reference to FIGS. 1-5. On the oral care implement 300, the depression 330 and the applicator 340 are located on a right-side surface of the handle portion 320 of the body 305.

However, the depression 330 and the applicator 340 can be located at any position as discussed above with regard to the oral care implement 100.

The oral care implement 300 also comprises a cover 360 that is coupled to the body 305 of the oral care implement 300 so as to be alterable between a storage state (see FIG. 7A) in which the depression 330 is enclosed by the cover 360 and a use state (see FIG. 7B) in which the floor 331 of the depression 330 and the exposed portion 345 of the applicator 340 is exposed. The main difference between the oral care implement 300 relative to the oral care implement 100 is the shape of the cover 360 and the manner in which the cover 360 is coupled to the handle portion 320 of the oral care implement 300.

Specifically, in the exemplified embodiment the cover 360 is a tubular member that is rotatably coupled to the body 305. Thus, the cover 360 is rotatable about the longitudinal axis E-E to alter the cover 360 between the storage and use states. Specifically, rotating the cover 360 in the direction of the arrow F of FIG. 7B alters the cover 360 from the storage state to the use state. Rotating the cover 360 in the direction of the arrow G of FIG. 7A alters the cover 360 from the use state to the storage state.

More specifically, the cover 360 comprises a first collar 371, a second collar 372 and a plate member 373 attached to each of the first and second collars 371, 372. The plate member 373 functions as a shroud to protect the applicator 340 when the cover 360 is in the storage state. The first and second collars 371, 372 are located on opposite sides of the depression 330 and each of the first and second collars 371, 372 are connected to opposing edges of the plate member 373 to form the tubular shape of the cover 360. Thus, although described herein as being tubular, the cover 360 may have a window or portion that is devoid of material extending in between the first and second collars 371, 372 in the direction of the longitudinal axis E-E.

Furthermore, the cover 360 and the handle portion 320 of the oral care implement 300 may include a protuberance/detent cooperation that prevents the cover 360 from rotating freely. Thus, the handle portion 320 may include a protuberance that cooperates with a detent on the interior surface of the cover 360 or the handle portion 320 may include a detent that cooperates with a protuberance on the interior surface of the cover 360. Thus, a user will have to apply rotational force to the cover 360 relative to the handle portion 320 of the oral care implement 300 in order to pull the protuberance out of the detent to allow for rotation of the cover 360 about the longitudinal axis E-E when it is desired to rotate the cover 360 between the storage and use states.

Referring to FIGS. 8-11 concurrently, an oral care implement 400 is illustrated in accordance with another embodiment of the present invention. The oral care implement 400 is similar to the oral care implement 100 in many respects, and thus similar features will be similarly numbered except that the 400-series of numbers will be used. Certain features of the oral care implement 400 may be similarly numbered as the oral care implement 100 but might not be described in detail herein in the interest of brevity, it being understood that the discussion of the similar component on the oral care implement 100 applies. Furthermore, features of the oral care implement 100 described above that are not illustrated on the oral care implement 400 or that are illustrated on the oral care implement 400 but not numbered are applicable to the oral care implement 400 in certain embodiments and vice versa. Thus, various combinations of the description below with regard to the oral care implement 400 and the description above with regard to the oral care implement 100 are within the scope of the present invention in some embodiments.

The oral care implement 400 is similar to the oral care implement 100 except that the cover 160 of the oral care implement 100 is replaced by a treatment device 460 that is detachably coupled to a body 405 of the oral care implement 400. Furthermore, the components and relative functions of the treatment device 460 and the handle portion 420 have been reversed. Specifically, in the oral care implement 400 the treatment device 460 comprises a store of oral care material 481, an applicator 440 and a bite guard 468. The handle portion 420 still comprises a depression 430, but also includes a slot 433 on the depression for accommodating the bite guard 468 of the treatment device. Moreover, in the exemplified embodiment the depression 430 is a convex surface and the applicator 440 on the treatment device 460 has a concave surface. These differences will be better understood from the description of FIGS. 8-11 below.

The oral care implement 400 generally comprises the body 405, which extends from a proximal end 401 to a distal end 402 along a longitudinal axis H-H. The body 405 generally comprises a handle portion 420 and a head portion 410. The handle portion 420 extends from a proximal end 421 (which is the same as the proximal end 401 of the body 405) to a distal end 422 and the head portion 410 is coupled to the distal end 422 of the handle portion. Furthermore, a plurality of tooth cleaning elements 415 extend from the head portion 410 of the body 405.

As noted above, the treatment device 460 is detachably coupled to the body 405. The oral care implement 400 is intended to be used such that the tooth cleaning elements 415 clean a user's teeth. Furthermore, the treatment device 460 is alterable between a storage state (FIGS. 8 and 10) and a use state (FIGS. 9 and 11), which will be described in more detail below. When the treatment device 460 is in the use state, the applicator 440 of the treatment device 460 is exposed and the applicator 440 can be used to apply or dispense an oral care material to a user's teeth or other surfaces of the user's oral cavity. When the treatment device 460 is in the storage state, the applicator 440 is not exposed and instead nests within the body 405 of the oral care implement 400. Specifically, the applicator 440 nests within the depression 430 between the treatment device 460 and the body 405 and is not visible. When the treatment device 460 is in the storage state, the treatment device 460 and the handle portion 420 of the body 405 collectively form a handle 429 that can be comfortably gripped by a user during toothbrushing.

As noted above, the handle portion 420 of the body 405 comprises a depression 430 within which the treatment device 460 nests when the treatment device 460 is in the storage state. In the exemplified embodiment, the depression 430 is located in a proximal section 403 of the handle portion 420 of the oral care implement 400. More specifically, the depression 430 is located adjacent the proximal end 421 of the handle portion 420 and extends to a location adjacent a thumb grip portion 426 of the handle portion 420. However, the invention is not to be so limited in all embodiments and the depression 430 may be positioned at other locations along the handle portion 420 of the body 405 and may extend for longer or shorter lengths along the handle portion 420. Furthermore, although in the exemplified embodiment the depression 430 is illustrated as being formed into the front surface of the handle portion 420, the invention is not to be so limited in all embodiments and in certain other embodiments the depression 430 may be formed into the rear surface of the handle portion 420 or any other portions (such as one of the right and left-side surfaces) of the outer surface 425 of the handle portion 420 as desired. In other embodiments the depression 430 may be located on the head portion 410. In the exemplified embodiment, the depression 430 forms a recess or cutout into the outer surface 425 of the handle portion 420 within which the treatment device 460 nests when the treatment device 460 is in the storage state.

In the exemplified embodiment, the depression 430 extends axially in a direction of the longitudinal axis H-H along a portion of the length of the handle portion 420 of the body 405. The depression 430 comprises a floor 431 and upstanding sidewalls 432 that extend from the floor 431 to the outer surface 425 of the handle portion 420. In the exemplified embodiment, the floor 431 of the depression 430 is convex along a direction of the longitudinal axis H-H. Of course, the invention is not to be so limited in all embodiments and in certain other embodiments the floor 431 of the depression 430 may be concave or flat. However, forming the floor 431 of the depression 430 as a convex surface facilitates cooperation between the treatment device 460 and the depression 430 when the treatment device 460 is in the storage state, as discussed in more detail below. The handle portion 420 also comprises a slot or aperture 433 formed into the floor 431 of the depression for accommodating the bite guard 468 of the treatment device 460 when the treatment device 468 is in the storage state. The slot or aperture 433 is elongated in the direction of the longitudinal axis H-H.

Figure 9:
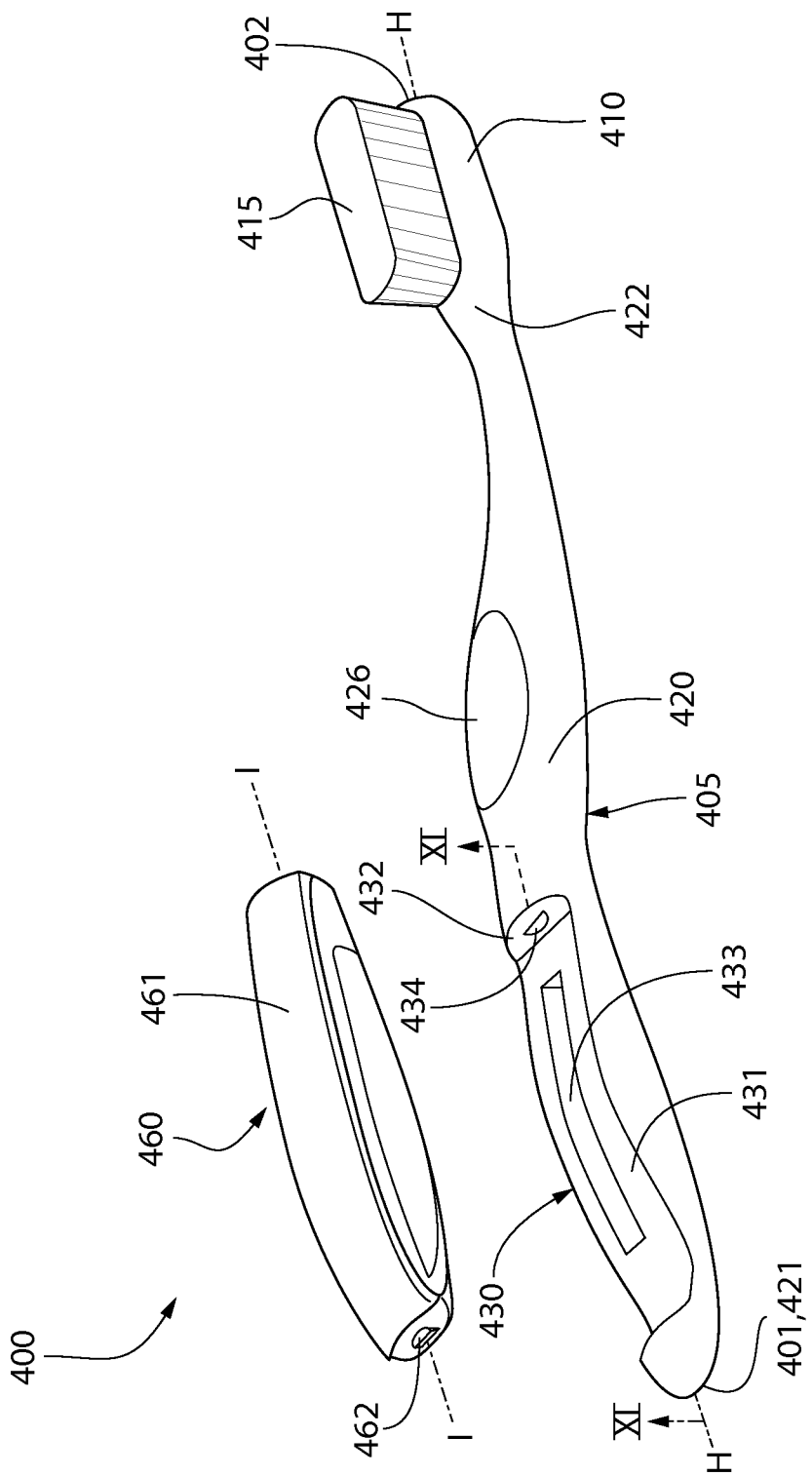
FIG. 9 is a perspective view of the toothbrush of FIG. 8 with the treatment device separated from the body.
Figure 10:
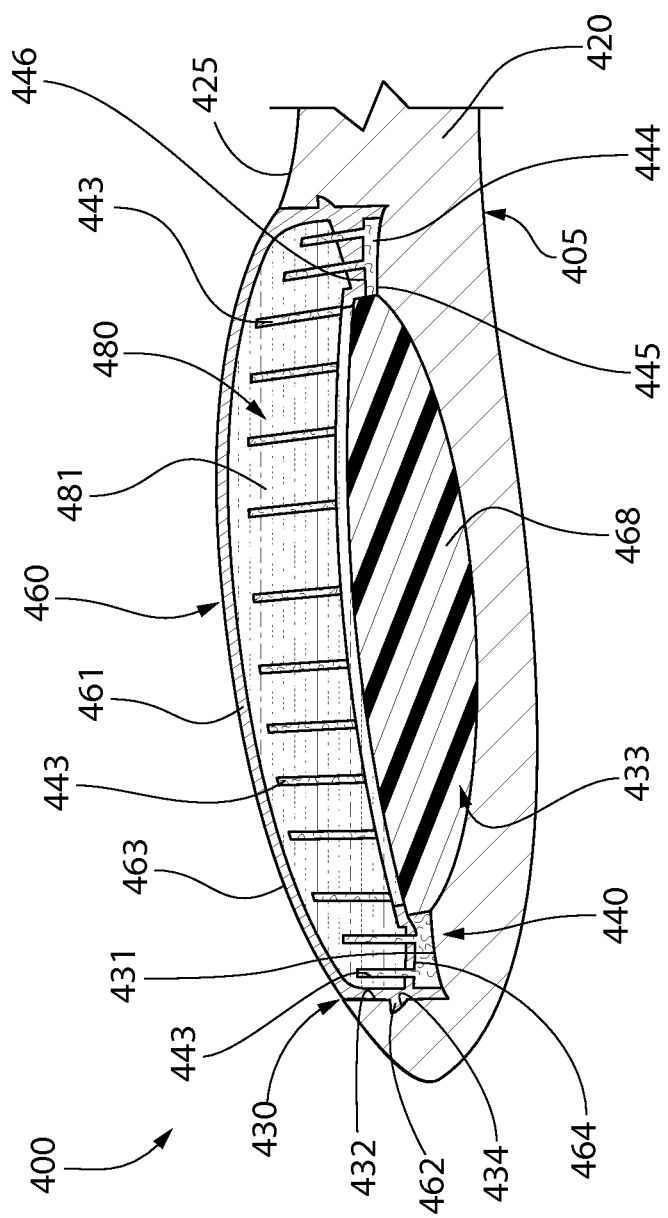
FIG. 10 is a cross-sectional view taken along line X-X of FIG. 8.
Figure 11:
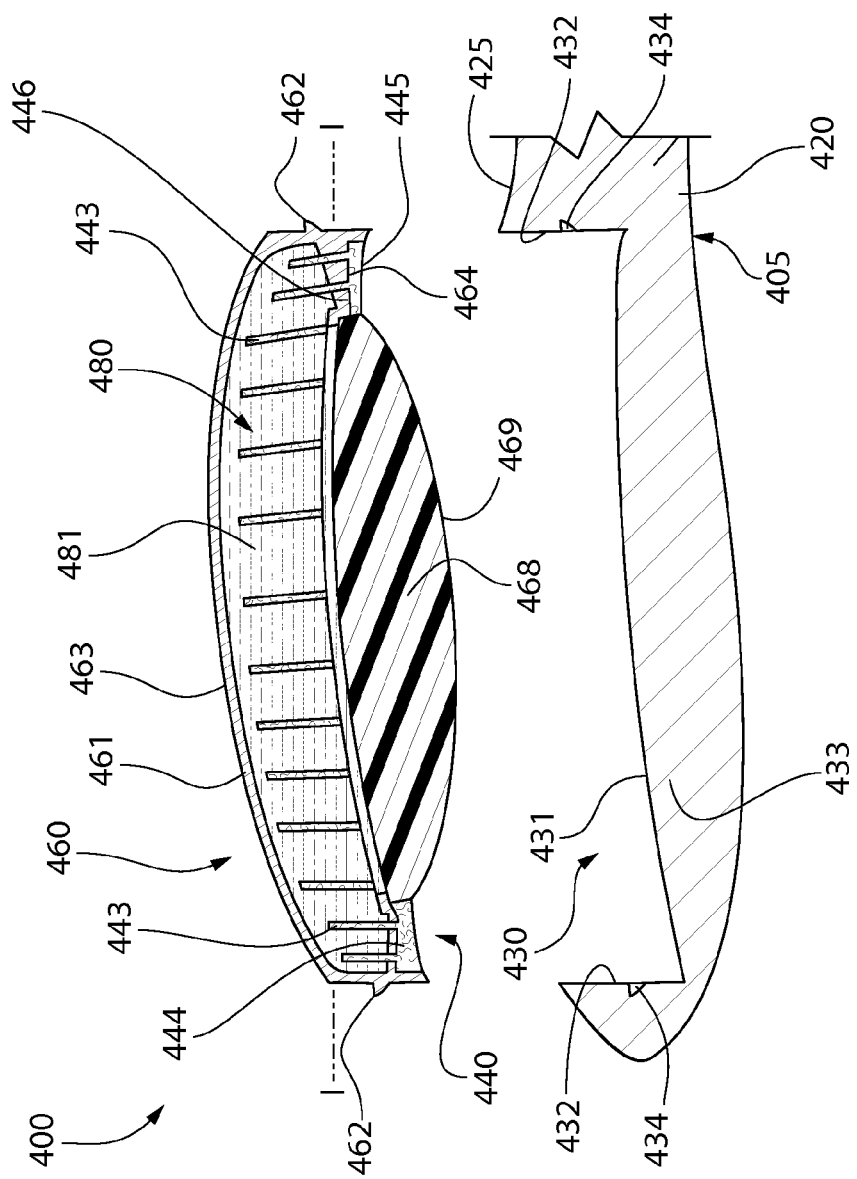
FIG. 11 is a cross-sectional view taken along line XI-XI of FIG. 9.

As noted above, the treatment device 460 is capable of dispensing or applying an oral care material onto a user's teeth or other oral surfaces. The treatment device 460 extends along a longitudinal axis I-I as depicted in FIGS. 9 and 11. Furthermore, the treatment device 460 comprises a housing 461, a store of oral care material 481 in the housing 461, and the applicator 440 which is fluidly coupled to the store of oral care material 481. Specifically, the housing 461 of the treatment device 460 defines a reservoir or hollow interior cavity 480 and the store of the oral care material 481 is located within the reservoir or hollow interior cavity 481 of the housing 461. The oral care material 481 can be any of one or more of the oral care materials 181 discussed above with regard to the oral care implement 100.

The housing 461 of the treatment device 460 comprises an outer surface 463 and an opposing inner surface 464. When the treatment device 460 is in the storage state, the treatment device 460 forms a transverse section of the handle 429 of the oral care implement 400 along the length of the depression 430. Furthermore, when the treatment device 460 is in the storage state, the outer surface 463 of the treatment device 460 is substantially flush with the outer surface 425 of the handle portion 420 of the body 405. This flush relationship provides for a more comfortable gripping surface for a user who is gripping the handle 429 to manipulate the oral care implement 400 during use.

In the exemplified embodiment, the applicator 440 is coupled to the housing 461 and comprises an exposed portion 445 that forms at least a portion of the inner surface 464 of the treatment device 460. However, the invention is not to be so limited and the applicator 440 may protrude from or be recessed relative to the inner surface 464 of the treatment device 460 in other embodiments. However, having the applicator 440 form a portion of the inner surface 464 of the treatment device 460 facilitates conformal surface contact between the applicator 440 and the facial surfaces of a user's teeth during use of the treatment device 460. In the exemplified embodiment, the exposed surface 445 of the applicator 440 is a concave surface. Thus, in such embodiments the applicator 440 comprises the concave exposed surface 445 that forms at least a portion of the inner surface 464 of the treatment device 460. Furthermore, in the exemplified embodiment the concave exposed surface 445 of the applicator 440 is concave in a direction along the longitudinal axis I-I.

As noted above, in some embodiments the treatment device 460 also comprises the bite guard 468 protruding from the housing 461. More specifically, the bite guard 468 protrudes from the inner surface 464 of the treatment device 460 (and of the housing 461 of the treatment device 460). The bite guard 468 in the exemplified embodiment has a semi-circular shape and terminates in a free edge 469. Of course, the invention is not to be so limited in all embodiments and the bite guard 468 can take on any other desired shape, such as the shapes discussed above with regard to the bite guard 168.

The bite guard 468 may be positioned adjacent to the applicator 440. In the exemplified embodiment the applicator 440 comprises a first applicator portion and a second applicator portion (not visible in the figures provided, but the illustration of FIGS. 2 and 5 adequately depicts this feature). Furthermore, in the exemplified embodiment the bite guard 468 is located between the first and second applicator portions. Each of the first and second applicator portions and the bite guard 468 is elongated in the direction of the longitudinal axis I-I. As a result of the relative positioning between the bite guard 468 and the first and second applicator portions, if the bite guard 468 is held between a user's teeth, the first applicator portion will be in contact with the facial surfaces of the user's upper teeth while the second applicator portion is simultaneously in contact with the facial surfaces of the user's lower teeth.

As noted above, the applicator 440 of the treatment device 460 is fluidly coupled to the store of oral care material 481 contained within the housing 461 of the treatment device 460. In the exemplified embodiment, the applicator 440 comprises a pad 444 formed of a capillary material. The capillary material of the pad 444 can be any of the materials discussed above with regard to the applicator 140. Of course, the applicator 440 can be formed of other materials such as rubber or a hard plastic as was discussed above with regard to the applicator 140. The applicator 440 comprises the exposed surface 445 and a non-exposed or bottom surface 446 opposite the exposed surface 445. As noted above, in the exemplified embodiment the exposed surface 445 of the applicator 440 forms at least a portion of the inner surface 464 of the treatment device 460. When the treatment device 460 is in the storage state, the exposed surface 445 of the applicator 440 is in surface contact with the floor 431 of the depression 430 and the bite guard 468 is positioned within the slot or aperture 433.

Furthermore, in the exemplified embodiment the pad 444 of the applicator 440 is not in direct contact with the store of oral care material 481. Thus, one or more wicking members 443 (only some of which are labeled in the drawings to avoid clutter) extend from the bottom surface 446 of the applicator 440 and into the store of the oral care material 481 to wick the oral care material 481 from the store and onto the pad 444 of the applicator 440. Via capillary action, the oral care material 481 wicks up through the wicking members 443 and onto the pad 444 of the applicator 440, where the oral care material 481 can be dispensed or applied to the user's teeth or other oral surfaces. Of course, the invention is not to be so limited in all embodiments and in certain other embodiments the bottom surface 446 of the pad 444 of the applicator 440 may be in direct contact with the store of the oral care material 481.

The exposed surface 445 of the applicator 440, and more specifically of the pad 444 of the applicator 440, preferably has a concave shape to facilitate directly contacting the facial surfaces of the user's teeth with the exposed surface 445 of the applicator 440. Thus, in certain embodiments the concave shape of the exposed surface 445 of the applicator 440 corresponds to the collective shape of the facial surfaces of the user's teeth, which may include only the labial surfaces or the labial and buccal surfaces of the user's teeth. Thus, during use as discussed in more detail below, the concave exposed surface 445 of the applicator 440 is sized and shaped to simultaneously contact the facial surfaces of a plurality (or all in some embodiments) of the user's teeth. In certain embodiments the entire inner surface 464 of the treatment device 460 is a concave surface.

When a user desires to use the oral care implement 400, first the treatment device 460 is in the storage state such that the treatment device 460 is nesting in the depression 430. In this position, the user will grip the handle 429 and insert the head portion 420 of the oral care implement 400 into his or her mouth to brush his or her teeth with the tooth cleaning elements 415. At any desired time (either before toothbrushing, after toothbrushing or at any other desired time including a time that is temporally remote from a toothbrushing session), the user may desire to apply the oral care material 481 to his or her teeth. Thus, at such desired times the user can detach the treatment device 460 from the body 405 of the oral care implement 400 to alter the treatment device 460 into the use state.

Once in the use state, the user can place the treatment device 460 up to his or her teeth such that the exposed portion 445 of the applicator 440 is in contact with the user's teeth. In this position, if the treatment device 460 includes the bite guard 468, the bite guard 468 can be held between the user's upper and lower teeth. As noted above, the exposed portion 445 of the applicator 440 has a concave shape with a contour that corresponds to the collective contour of the facial surfaces of the user's teeth. Thus, the applicator 440 is positioned into contact with a plurality (or all) of the facial surfaces of the user's teeth simultaneously. When the applicator 440 is positioned into contact with the facial surfaces of the user's teeth, the oral care material 481 is dispensed from the applicator 440 to the facial surfaces of the user's teeth to impart a desired hygienic benefit, such as tooth whitening, to the user's teeth.

After the applicator 440 has been held into contact with the user's teeth for a desired period of time, the treatment device 460 is pulled away from the user's mouth and the treatment device is then put back into the storage state. In the exemplified embodiment, in the storage state connectors 462 of the treatment device 460 cooperate with connectors 432 on the sidewalls 432 of the handle portion 420 of the oral care implement 400 to secure the treatment device 460 to the body 405 in the storage state. Of course, as discussed above in other embodiments the connectors 432, 464 may be omitted and the treatment device 460 may couple to the body 405 via an interference fit, a friction fit or the like.

Thus, both in the embodiment of the oral care implement 100 and the oral care implement 400, an oral care material can be applied to a plurality of a user's teeth simultaneously. In previous oral care implements that included an oral care material dispensing system or device, the applicator had a dispensing surface capable of applying the oral care material onto a single tooth surface at a time. By shaping the applicator to have a concave dispensing surface, the present invention is able to speed up the delivery time by applying the oral care material onto a plurality (or all) of the user's teeth simultaneously. Furthermore, due to the capillary material of the applicators, the oral care material can be dispensed passively without requiring the user to activate a pump or actuator, although as discussed above an actuator can be used in some embodiments. Furthermore, by maintaining the oral care material within the body of the oral care implement or within a treatment device that is detachably coupled to the body of the oral care implement, all of the materials needed for toothbrushing and oral care material application are available in a single device.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A toothbrush comprising:
   a body comprising a handle portion and a head portion;
   a plurality of tooth cleaning elements extending from the head portion; and
   a treatment device detachably coupled to the body so as to be alterable between a storage state and a use state, the treatment device comprising:
   a housing;
   a store of an oral care material in the housing;
   an applicator fluidly coupled to the store of the oral care material; and
   a bite guard protruding from the housing adjacent the applicator;
   wherein the applicator comprises a first applicator portion and a second applicator portion, the bite guard located between the first and second applicator portions.

2. The toothbrush according to claim 1 wherein the handle portion of the body comprises a depression, the treatment device nesting in the depression when the treatment device is in the storage state.

3. The toothbrush according to claim 2 wherein an outer surface of the treatment device is substantially flush with an outer surface of the handle portion of the body when the treatment device is in the storage state.

4. The toothbrush according to claim 2 wherein the handle portion comprises an aperture formed into a floor of the depression, the bite guard extending into the aperture when the treatment device is in the storage state.

5. The toothbrush according to claim 1 wherein the bite guard terminates in a free edge.

6. The toothbrush according to claim 1 wherein the bite guard protrudes from a concave inner surface of the treatment device.

7. The toothbrush according to claim 6 wherein the applicator comprises an exposed surface that forms at least a portion of the inner surface of the treatment device.

8. The toothbrush according to claim 1 wherein the applicator comprises a pad comprising a capillary material.

9. The toothbrush according to claim 8 further comprising one or more wicking members fluidly coupling the store of the oral care material to the applicator.

10. The toothbrush according to claim 1 wherein the housing comprises a reservoir containing the store of the oral care material.

11. A toothbrush comprising:
a body comprising a handle portion and a head portion;
a plurality of tooth cleaning elements extending from the head portion; and
a treatment device detachably coupled to the body so as to be alterable between a storage state and a use state, the treatment device comprising:
a housing;
a store of an oral care material in the housing;
an applicator fluidly coupled to the store of the oral care material; and
a bite guard protruding from the housing adjacent the applicator;
wherein the body comprises a depression having a convex floor, the treatment device nesting in the depression when the treatment device is in the storage state such that a concave inner surface of the treatment device is in surface contact with the floor of the depression when the treatment device is in the storage state.

12. A toothbrush comprising:
a body comprising a handle portion and a head portion;
a plurality of tooth cleaning elements extending from the head portion; and
a treatment device detachably coupled to the body so as to be alterable between a storage state and a use state, the treatment device comprising:
a housing;
a store of an oral care material in the housing; and
an applicator fluidly coupled to the store of the oral care material, the applicator comprising a concave exposed surface that forms at least a portion of an inner surface of the treatment device.

13. The toothbrush according to claim 12 wherein the handle portion of the body comprises a depression, the treatment device nesting in the depression when the treatment device is in the storage state.

14. The toothbrush according to claim 13 wherein the housing of the treatment device forms a transverse section of the handle of the toothbrush along the length of the depression when the treatment device is in the storage state.

15. The toothbrush according to claim 13 wherein the depression is located in a proximal section of the handle portion, the head portion coupled to a distal end of the handle portion.

16. The toothbrush according to claim 12 wherein the concave exposed surface of the applicator comprises a contour that corresponds to a collection of facial surfaces of a user's teeth.

17. The toothbrush according to claim 12 wherein the applicator comprises a pad comprising a capillary material.

18. The toothbrush according to claim 12 wherein the body comprises a depression having a convex floor, the treatment device nesting in the depression when the treatment device is in the storage state such that the concave exposed surface of the applicator is in surface contact with the floor of the depression when the treatment device is in the storage state.

19. The toothbrush according to claim 12 wherein the treatment device extends along a longitudinal axis, the concave exposed surface of the applicator being concave in a direction along the longitudinal axis.

* * * * *